(12) United States Patent
Ueno et al.

(10) Patent No.: US 11,129,974 B2
(45) Date of Patent: Sep. 28, 2021

(54) FINE HOLLOW PROTRUSION IMPLEMENT

(71) Applicant: KAO CORPORATION, Tokyo (JP)

(72) Inventors: Satoshi Ueno, Utsunomiya (JP); Takatoshi Niitsu, Utsunomiya (JP); Hideo Kobayashi, Moka (JP)

(73) Assignee: KAO CORPORATION, Tokyo (JP)

(*) Notice: Subject to any disclaimer, the term of this patent is extended or adjusted under 35 U.S.C. 154(b) by 343 days.

(21) Appl. No.: 16/089,583

(22) PCT Filed: Mar. 30, 2017

(86) PCT No.: PCT/JP2017/013140
§ 371 (c)(1),
(2) Date: Sep. 28, 2018

(87) PCT Pub. No.: WO2017/170815
PCT Pub. Date: Oct. 5, 2017

(65) Prior Publication Data
US 2020/0306517 A1    Oct. 1, 2020

(30) Foreign Application Priority Data

Mar. 31, 2016 (JP) .............................. JP2016-071371

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01); *A61M 2037/0053* (2013.01)

(58) Field of Classification Search
CPC ...... A61M 37/0015; A61M 2037/0023; A61M 2037/003; A61M 2037/0053; A61M 2037/0061
See application file for complete search history.

(56) References Cited

U.S. PATENT DOCUMENTS 6,132,755 A   10/2000   Eicher et al.
6,256,533 B1   7/2001   Yuzhakov et al.
(Continued)

FOREIGN PATENT DOCUMENTS

CN   1310755 A   8/2001
CN   1432812 A   7/2003
(Continued)

OTHER PUBLICATIONS

International Search Report (PCT/ISA/210) issued in PCT/JP2017/013140, dated Jun. 13, 2017.

*Primary Examiner* — Amber R Stiles
(74) *Attorney, Agent, or Firm* — Birch, Stewart, Kolasch & Birch, LLP (57) ABSTRACT

The present invention provides a fine hollow protruding tool (1) having a basal member (2) and a fine hollow protrusions (3) project from the basal member (2). The fine hollow protrusions (3) each has an opening portion (3h) on a tip side thereof and an interior in which an interior space linked to the opening portion (3h) is formed. In any vertical cross-section passing through an apex of the fine hollow protrusion (3), a wall thickness (T1) in an apex-side region (TB) on the apex side is thinner than a wall thickness (T2) in a lower-side region (BP) that is closer to the basal member (2) than the apex-side region (TB) is, and a gap (M1c) between inner walls (31) in the apex-side region (TB) is smaller than a gap (M2c) between the inner walls (31) in the lower-side region (BP). A base portion (34) of the fine hollow protrusion (3) projecting from the basal member (2) has a curvature. An entrance portion (23) to the fine hollow protrusion (3), on a back face (25) of the basal member (2) opposite from a front face (24) from which the fine hollow protrusions (3) project, has a curvature.

25 Claims, 4 Drawing Sheets

(56) References Cited

U.S. PATENT DOCUMENTS

| | | |
|---|---|---|
| 6,379,324 B1 | 4/2002 | Gartstein et al. |
| 6,406,638 B1 | 6/2002 | Stoeber et al. |
| 6,931,277 B1 | 8/2005 | Yuzhakov et al. |
| 2002/0187556 A1 | 12/2002 | Shartle et al. |
| 2003/0045837 A1* | 3/2003 | Delmore .......... A61B 5/150022 604/173 |
| 2004/0220535 A1 | 11/2004 | Canham |
| 2004/0249310 A1 | 12/2004 | Shartle et al. |
| 2005/0209565 A1 | 9/2005 | Yuzhakov et al. |
| 2007/0078376 A1 | 4/2007 | Smith |
| 2010/0114043 A1* | 5/2010 | Jung ................ A61M 37/0015 604/272 |
| 2011/0213335 A1 | 9/2011 | Burton et al. |
| 2013/0116523 A1* | 5/2013 | Jung ....................... B29C 41/36 600/345 |
| 2014/0176568 A1 | 6/2014 | Bastos et al. |
| 2016/0158514 A1 | 6/2016 | Stoeber et al. |
| 2016/0354591 A1 | 12/2016 | Ueno |
| 2017/0057124 A1 | 3/2017 | Wakamatsu et al. |
| 2017/0239855 A1 | 8/2017 | Niitsu et al. |
| 2017/0312489 A1 | 11/2017 | Stoeber et al. |

FOREIGN PATENT DOCUMENTS

| | | |
|---|---|---|
| CN | 105217565 A | 1/2016 |
| CN | 105451911 A | 3/2016 |
| JP | 11-509123 A | 8/1999 |
| JP | 2003-501162 A | 1/2003 |
| JP | 2003-501163 A | 1/2003 |
| JP | 2003-519014 A | 6/2003 |
| JP | 2009-509634 A | 3/2009 |
| JP | 2014-176568 A | 9/2014 |
| JP | 2015-2860 | 1/2015 |
| JP | 2015-217042 A | 12/2016 |
| JP | 2017-35432 A | 2/2017 |
| JP | 2017-38903 A | 2/2017 |
| JP | 2017-38904 A | 2/2017 |
| WO | WO 2004/110717 A2 | 12/2004 |
| WO | WO 2012/125122 A1 | 9/2012 |
| WO | WO 2013/171907 A1 | 11/2013 |
| WO | WO 2015/009530 A1 | 1/2015 |
| WO | WO 2015/129894 A1 | 9/2015 |
| WO | WO 2015/164840 A1 | 10/2015 |

\* cited by examiner

FINE HOLLOW PROTRUSION IMPLEMENT

TECHNICAL FIELD

The present invention relates to a fine hollow protruding tool.

BACKGROUND ART

Recently, the delivery of agents using microneedles has been gaining attention in the medical field and the beauty field. When using microneedles to pierce the skin to a shallow layer, the same performance as that when delivering agents using syringes can be achieved without inducing pain. Among microneedles, in particular, microneedles with opening portions are effective because they can increase the number of choices of agents to be provided inside the microneedles. Particularly when used in the medical or beauty field, microneedles with opening portions need to be able to pierce skin with minimum pain, and to be unlikely to break.

Examples of microneedles with opening portions include microneedles described in Patent Documents 1 and 2. Patent Document 1 describes microneedles whose tip portions respectively have inclined faces that are inclined. Furthermore, Patent Document 1 states that the microneedles whose tip portions respectively have inclined faces are manufactured through known injection molding.

Furthermore, Patent Document 2 describes hollow microneedles having average channel holes with a length of less than 1 mm and a cross-sectional area of 20 to 50 $\mu m^2$. Furthermore, Patent Document 2 states that the hollow microneedles having average channel holes are manufactured by forming solid microneedles through heat cycle injection molding, and then forming channel holes through laser drilling.

CITATION LIST

Patent Literature

Patent Literature 1: US 2014176568(A1)
Patent Literature 2: US 2011213335(A1)

SUMMARY OF INVENTION

The present invention is directed to a fine hollow protruding tool comprising a basal member and a fine hollow protrusion which project from the basal member. The fine hollow protrusion has an opening portion on a tip side thereof and an interior space formed to link to the opening portion. In any vertical cross-section passing through an apex of the fine hollow protrusion, a wall thickness in an apex-side region on the apex side is thinner than a wall thickness in a lower-side region that is closer to the basal member than the apex-side region, and a gap between inner walls in the apex-side region is smaller than a gap between the inner walls in the lower-side region, a base portion of the fine hollow protrusion projecting from the basal member has a curvature, and an entrance portion to the fine hollow protrusion, on an opposite face of the basal member opposite from a face from which the fine hollow protrusion projects, has a curvature.

BRIEF DESCRIPTION OF DRAWINGS

FIGS. 5(a) to 5(e) are views illustrating steps for manufacturing a fine hollow protruding tool having opening portions using the manufacturing apparatus shown in FIG. 4.

DESCRIPTION OF EMBODIMENTS

According to the manufacturing method through known injection molding described in Patent Document 1, the wall thickness of tip portions of microneedles cannot be made thin, and the tip portions cannot be made sharp, and thus it is difficult to reduce pain when piercing the skin. Furthermore, Patent Document 1 does not include anything about a relationship between the wall thickness on the tip side and the wall thickness on the base side, or anything about breakability.

Furthermore, according to the manufacturing method described in Patent Document 2, after solid microneedles have been formed, channel holes are formed through laser drilling, and thus a processing margin is necessary for the tip portions. Accordingly, the tip portions cannot be made sharp, and thus it is difficult to reduce pain when piercing the skin. Furthermore, as in Patent Document 1, Patent Document 2 does not include anything about a relationship between the wall thickness on the tip side and the wall thickness on the base side, or anything about breakability.

The present invention relates to a fine hollow protruding tool having opening portions that can solve the above-mentioned problems in the related art.

Figure 1:
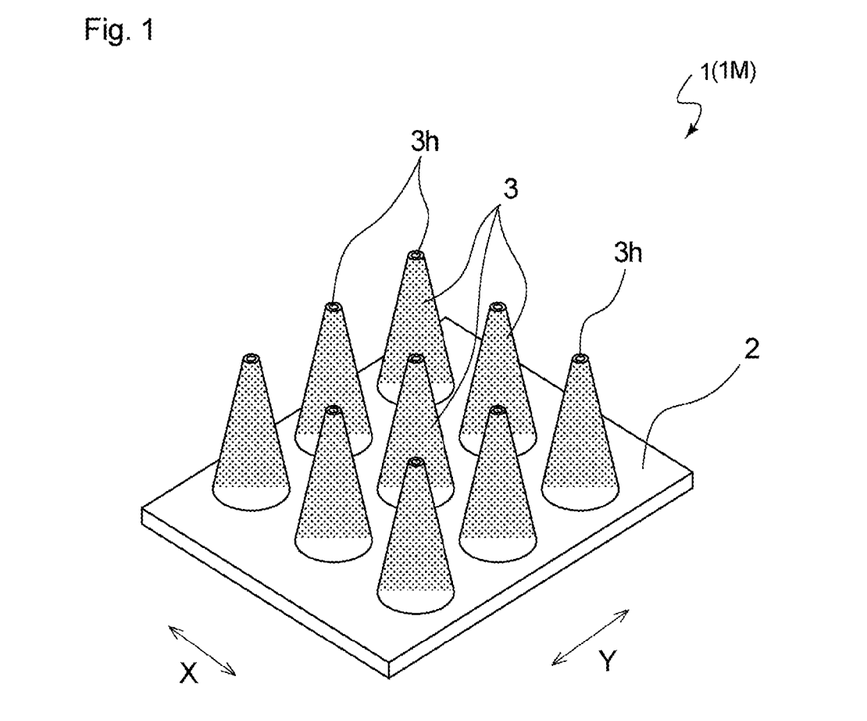
FIG. 1 is a schematic perspective view of a fine hollow protruding tool according to a preferable embodiment of a fine hollow protruding tool having opening portions of the present invention.

Hereinafter, a fine hollow protruding tool of the present invention will be described with reference to the drawings based on a fine hollow protruding tool 1 according to a preferable first embodiment. FIG. 1 shows a perspective view of a microneedle array 1M as the fine hollow protruding tool 1 of the first embodiment. The microneedle array 1M of the first embodiment has a form in which fine hollow protrusions 3 project from a basal member 2, the fine hollow protrusions 3 each having an opening portion 3h on the tip side, and an interior in which an interior space linked to the opening portion 3h is formed. In the first embodiment, as shown in FIG. 1, the microneedle array 1M includes a sheet-like basal member 2 and a plurality of fine hollow protrusions 3. There is no particular limitation on the number of fine hollow protrusions 3, the arrangement of the fine hollow protrusions 3, and the shape of the fine hollow protrusions 3, but, in the microneedle array 1M of the first embodiment, it is preferable that nine truncated conical fine hollow protrusions 3 are arranged in an array on the upper face of the sheet-like basal member 2. The nine fine hollow protrusions 3 arranged in an array are arranged in three rows along a Y direction, which is the direction in which a later-described base material sheet 2A is transported (i.e., the longitudinal direction of the basal member 2), and in three columns along an X direction, which is the direction orthogonal to the transporting direction and which is the lateral direction of the basal member 2.

Figure 2:
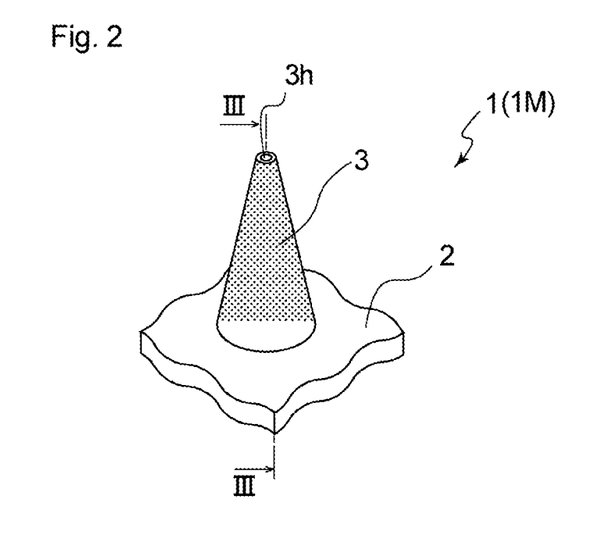
FIG. 2 is a perspective view of the fine hollow protruding tool focusing on one fine hollow protrusion shown in FIG. 1.
Figure 3:
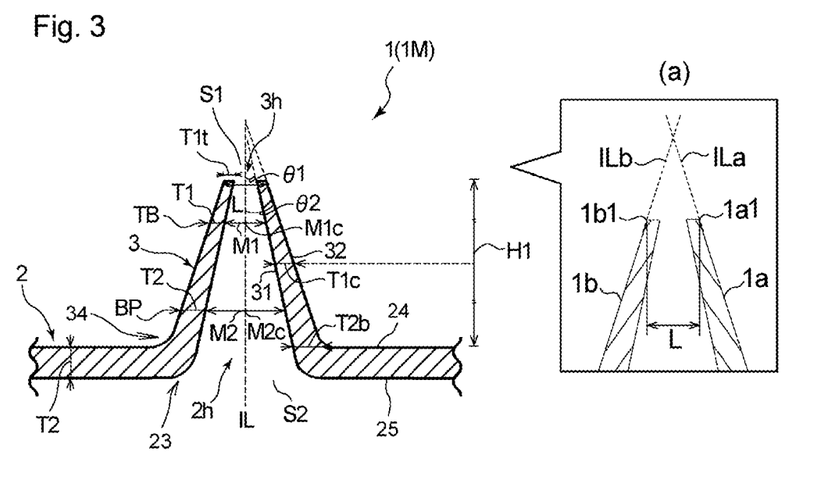
FIG. 3 is a cross-sectional view taken along line shown in FIG. 2.

Note that FIG. 2 is a perspective view of the microneedle array 1M focusing on one fine hollow protrusion 3 from among the fine hollow protrusions 3 arranged in an array included in the microneedle array 1M. Furthermore, FIG. 3 is a cross-sectional view taken along line III-III shown in FIG. 2, and is a vertical cross-sectional view passing through the apex of a fine hollow protrusion 3. In the case where an opening portion 3h is provided at the tip on the tip side of the fine hollow protrusion 3 as in the microneedle array 1M of the first embodiment, the apex of the fine hollow protrusion 3 refers to the center of the opening portion 3h.

It is sufficient that the opening portions 3h are provided on the tip side of the fine hollow protrusions 3. In the microneedle array 1M of the first embodiment, the opening portions 3h are provided at the tips of the fine hollow protrusions 3 as shown in FIGS. 2 and 3. Preferably, in the first embodiment, the fine hollow protrusions 3 are such that interior spaces extending from the lower face of the basal member 2 to the opening portions 3h are formed in the interior of the fine hollow protrusions 3, and the opening portions 3h are formed at the tips of the fine hollow protrusions 3, as shown in FIG. 3. In the first embodiment, the fine hollow protrusions 3 are such that inner walls 31 defining the interior portion are formed in the shape of straight lines, and outer walls 32 forming the outer shape are formed in the shape of straight lines, in a vertical cross-section as shown in FIG. 3. In the microneedle array 1M, the interior spaces of the fine hollow protrusions 3 are formed in a shape that conforms to the outer shape of the fine hollow protrusions 3, and, in the first embodiment, they are formed in a truncated conical shape, which is a shape that conforms to the outer shape of the truncated conical fine hollow protrusions 3. Note that, although the interior spaces of the fine hollow protrusions 3 are in a truncated conical shape in the first embodiment, they may be a truncated pyramidal shape or the like instead of a truncated conical shape.

The microneedle array 1M is such that, in any vertical cross-section passing through the apex of a fine hollow protrusion 3 (see FIG. 3), a wall thickness T1 in an apex-side region TB on the apex side is smaller than a wall thickness T2 in a lower-side region BP that is closer to the basal member 2 than the apex-side region TB is, a gap M1 between the inner walls 31, 31 in the apex-side region TB is smaller than a gap M2 between the inner walls 31, 31 in the lower-side region BP, a base portion 34 of the fine hollow protrusion 3 projecting from the basal member 2 has a curvature, and an entrance portion 23 to the fine hollow protrusion 3 on a back face 25, which is an opposite face that is opposite from a front face 24, has a curvature, the front face 24 being a face of the basal member 2 from which the fine hollow protrusion 3 projects. Here, the base portion 34 is a portion projecting from the basal member 2, and, in the microneedle array 1M of this embodiment, the base portion 34 is a portion projecting from the front face 24 of the basal member 2.

Preferably, the microneedle array 1M of the first embodiment is such that the interior spaces and the outer shapes of the fine hollow protrusions 3 are formed in a truncated conical shape, and the tips of the fine hollow protrusions 3 respectively have the opening portions 3h, and thus, in the microneedle array 1M, in any vertical cross-section passing through the apex of a fine hollow protrusion 3 (the center of the opening portion 3h at the tip), the wall thickness T1 in the apex-side region TB is thinner than the wall thickness T2 in the lower-side region BP, and the gap M1 between the inner walls 31, 31 in the apex-side region TB is smaller than the gap M2 between the inner walls 31, 31 in the lower-side region BP. In this manner, the wall thickness T1 in the apex-side region TB is thinner than the wall thickness T2 in the lower-side region BP, and the gap M1 between the inner walls 31, 31 in the apex-side region TB is smaller than the gap M2 between the inner walls 31, 31 in the lower-side region BP, and thus the microneedle array 1M can be used to pierce the skin with less pain, and is unlikely to break.

Furthermore, preferably, the microneedle array 1M of the first embodiment is such that the base portion 34 of the fine hollow protrusion 3 projecting from the front face 24 of the basal member 2 is curved with a curvature. Specifically, the microneedle array 1M of the first embodiment is such that the base portion 34 of the fine hollow protrusion 3 on the front face 24 side of the basal member 2 is curved with a curvature. In this manner, the base portion 34 of the fine hollow protrusion 3 has a curvature, and thus the microneedle array 1M is less likely to break.

Furthermore, preferably, the microneedle array 1M of the first embodiment is such that the entrance portion 23 to the fine hollow protrusion 3 on the back face 25 side of the basal member 2 is curved with a curvature. In this manner, the entrance portion 23 to the fine hollow protrusion 3 on the back face 25 side of the basal member 2 has a curvature, and thus the flowing of agents during delivery of the agents is facilitated.

Note that, if the interior spaces and the outer shapes of the fine hollow protrusions 3 are formed in a truncated pyramidal shape, a vertical cross-section passing through the apex of a fine hollow protrusion 3 in the microneedle array 1M is preferably taken at a position not passing through any corner of the truncated pyramidal shape.

The microneedle array 1M of the first embodiment is such that the interior spaces and the outer shapes of the fine hollow protrusions 3 are formed in a truncated conical shape, and the tips of the fine hollow protrusions 3 respectively have the opening portions 3h, and thus, in the microneedle array 1M of the first embodiment, an inner peripheral shape defined by the inner wall 31 in a horizontal cross-section in the apex-side region TB is similar to an inner peripheral shape defined by the inner wall 31 in a horizontal cross-section in the lower-side region BP. Furthermore, in the microneedle array 1M, an outer peripheral shape defined by the outer wall 32 in a horizontal cross-section in the apex-side region TB is similar to an outer peripheral shape defined by the outer wall 32 in a horizontal cross-section in the lower-side region BP. Since the microneedle array 1M is formed in this manner, it is less likely to break. Furthermore, as described above, in the microneedle array 1M of the first embodiment, the interior spaces and the outer shapes of the fine hollow protrusions 3 are formed in a truncated conical shape as shown in FIG. 2, and thus a circular shape defined by the inner wall 31 in a horizontal cross-section in the apex-side region TB is concentric with a circular shape defined by the inner wall 31 in a horizontal cross-section in the lower-side region BP. Since the microneedle array 1M is formed in this manner, it is less likely to break.

Furthermore, the microneedle array 1M is such that, in any vertical cross-section passing through the apex of a fine hollow protrusion 3 (see FIG. 3), an angle θ2 formed between a perpendicular line IL passing through the apex and the outer wall 32 of the fine hollow protrusion 3 is larger than an angle θ1 formed between the perpendicular line IL and the inner wall 31 of the fine hollow protrusion 3. Preferably, the microneedle array 1M of the first embodiment is such that the interior spaces and the outer shapes of the fine hollow protrusions 3 are formed in a truncated conical shape, and the tips of the fine hollow protrusions 3 respectively have the opening portions 3h, and thus, in the microneedle array 1M, in any vertical cross-section passing through the apex of a fine hollow protrusion 3 (the center of the opening portion 3h at the tip), the angle θ2 formed between the perpendicular line IL passing through the apex and the outer wall 32 is larger than the angle θ1 formed between the perpendicular line IL and the inner wall 31. Since the microneedle array 1M is formed in this manner, it is possible to further reduce pain when piercing the skin. Furthermore, flowing of agents is facilitated during delivery through the microneedle array 1M.

In order to reduce pain when piercing the skin and to facilitate delivery of agents, a ratio (θ2/θ1) of the angle θ2 formed between the perpendicular line IL and the outer wall 32 with respect to the angle θ1 formed between the perpendicular line IL and the inner wall 31 is preferably 0.03 or greater, and more preferably 0.1 or greater, is preferably 90 or less, and more preferably 45 or less, and, specifically, is preferably from 0.03 to 90, and more preferably from 0.1 to 45. The angle θ1 is preferably 0.5 degrees or greater, and more preferably 2.5 degrees or greater, is preferably 30 degrees or less, and more preferably 22.5 degrees or less, and, specifically, is preferably from 0.5 to 30 degrees, and more preferably from 2.5 to 22.5 degrees or less. Furthermore, the angle θ2 is preferably 1 degree or greater, and more preferably 3 degrees or greater, is preferably 45 degrees or less, and more preferably 30 degrees or less, and, specifically, is preferably from 1 to 45 degrees, and more preferably from 3 to 30 degrees. The angles θ1 and θ2 are observed in a vertical cross-section passing through the apex of the fine hollow protrusion 3 enlarged at a predetermined magnification using a scanning electron microscope (SEM) or a microscope.

Furthermore, the microneedle array 1M is such that, in any vertical cross-section passing through the apex of a fine hollow protrusion 3 (see FIG. 3), the perpendicular line IL passing through the apex passes through an apex-side center position M1c at which the gap M1 between the inner walls 31, 31 in the apex-side region TB is halved and a lower-side center position M2c at which the gap M2 between the inner walls 31, 31 in the lower-side region BP is halved. Preferably, the microneedle array 1M of the first embodiment is such that the interior spaces and the outer shapes of the fine hollow protrusions 3 are formed in a truncated conical shape, and the tips of the fine hollow protrusions 3 respectively have the opening portions 3h, and thus, in the microneedle array 1M, in any vertical cross-section passing through the apex of a fine hollow protrusion 3 (the center of the opening portion 3h at the tip), the perpendicular line IL passing through the apex passes through the apex-side center position M1c and the lower-side center position M2c. Since the microneedle array 1M is formed in this manner, it is less likely to break.

Furthermore, in the microneedle array 1M of the first embodiment, the wall thickness T1 in the apex-side region TB is uniform around the entire circumference. Preferably, the microneedle array 1M of the first embodiment is such that the tips of the fine hollow protrusions 3 respectively have the opening portions 3h, and the interior spaces and the outer shapes of the fine hollow protrusions 3 are formed in a truncated conical shape, and thus, at each tip in the microneedle array 1M, the inner periphery defined by the inner wall 31 and the outer periphery defined by the outer wall 32 are each in a circular shape. Thus, a wall thickness T1t at the tip, in other words, the gap between the circular inner periphery and the circular outer periphery is uniform around the entire circumference. Since the microneedle array 1M is formed in this manner, it is less likely to break.

Each fine hollow protrusion 3 in the microneedle array 1M of the first embodiment is inserted such that its tip reaches the stratum corneum, which is the outermost layer, or the dermis, which is a deeper layer, and thus a projecting height H1 thereof is preferably 0.01 mm or greater, and more preferably 0.02 mm or greater, is preferably 10 mm or less, and more preferably 5 mm or less, and, specifically, is preferably from 0.01 to 10 mm, and more preferably from 0.02 to 5 mm.

The fine hollow protrusions 3 in the microneedle array 1M of the first embodiment each have a wall thickness T1t at the tip that is preferably 0.001 mm or greater, and more preferably 0.003 mm or greater, is preferably 0.005 mm or less, and more preferably 0.1 mm or less, and, specifically, is preferably from 0.001 to 0.1 mm, and more preferably from 0.003 to 0.05 mm, in order to reduce pain when piercing the skin.

The fine hollow protrusions 3 in the microneedle array 1M of the first embodiment each have a wall thickness T1c, at a position where the projecting height H1 is halved, that is preferably 0.001 mm or greater, and more preferably 0.003 mm or greater, is preferably 0.1 mm or less, and more preferably 0.05 mm or less, and, specifically, is preferably from 0.001 to 0.1 mm, and more preferably from 0.003 to 0.05 mm, in order to reduce pain when piercing the skin and to make the fine hollow protrusions 3 unlikely to break.

The fine hollow protrusions 3 in the microneedle array 1M of the first embodiment each have a wall thickness T2b, on the upper face of the basal member 2, that is preferably 0.004 mm or greater, and more preferably 0.008 mm or greater, is preferably 0.4 mm or less, and more preferably 0.25 mm or less, and, specifically, is preferably from 0.004 to 0.4 mm, and more preferably from 0.008 to 0.25 mm, in order to make the fine hollow protrusions 3 unlikely to break when piercing the skin.

The tips of the fine hollow protrusions 3 in the microneedle array 1M each have a tip diameter L (the gap between the outer walls 32, 32 at the tip) that is preferably 1 μm or greater, and more preferably 5 μm or greater, is preferably 500 μm or less, and more preferably 300 μm or less, and, specifically, is preferably from 1 to 500 μm, and more preferably from 5 to 300 μm. The tip diameter L of the fine hollow protruding tool 1 is the length at a position where the length is longest at the tip of a fine hollow protrusion 3. If the tip diameter L is within the above-described range, there is almost no pain when the microneedle array 1M is inserted into the skin. The tip diameter L is measured as follows.

Measurement of Tip Diameter of Fine Hollow Protrusions 3 in Microneedle Array 1M In the case where the tip of a fine hollow protrusion 3 is open, the tip portion of the fine hollow protrusion 3 is observed, for example, in an SEM image enlarged at a predetermined magnification (see FIG. 3(a)) using a scanning electron microscope (SEM) or a microscope.

Next, assuming that there is the tip of the fine hollow protrusion 3, an imaginary straight line ILa is extended along the straight-line portion of one lateral side 1a of two lateral sides 1a and 1b defining the outer walls 32, an imaginary straight line ILb is extended along the straight-line portion of the other lateral side 1b, and the point where they intersect is taken as the apex of the fine hollow protrusion 3. Next, the point where the lateral side 1a separates from the imaginary straight line ILa on the tip side is obtained as a first tip point 1a1, and the point where the other lateral side 1b separates from the imaginary straight line ILb is obtained as a second tip point 1b1. A length L of a straight line that links the thus obtained first tip point 1a1 and second tip point 1b1 is measured using a scanning electron microscope (SEM) or a microscope, and the measured length of the straight line is taken as the tip diameter of the fine hollow protrusion 3. Note that, in the case where the tip of a fine hollow protrusion 3 is not open, a point where the lateral side 1a separates from the imaginary straight line ILa is obtained as a first tip point 1a1, the point where the other lateral side 1b separates from the imaginary straight line ILb is obtained as a second tip point 1b1, and the tip diameter is measured using the above-described method.

The basal member 2 has a thickness T2 that is preferably 0.01 mm or greater, and more preferably 0.02 mm or greater, is preferably 1.0 mm or less, and more preferably 0.7 mm or less, and, specifically, is preferably from 0.01 to 1.0 mm, and more preferably from 0.02 to 0.7 mm.

As shown in FIG. 3, the fine hollow protruding tool 1 includes an opening portion 3h located at the tip of each fine hollow protrusion 3, and a basal-side opening portion 2h located in the lower face of the basal member 2 corresponding to each of the fine hollow protrusion 3. In the microneedle array 1M of the first embodiment, the opening portion 3h is concentric with the basal-side opening portion 2h.

Furthermore, the entrance portion 23 to the fine hollow protrusion 3 on the back face 25 side of the basal member 2, and the base portion 34 of the fine hollow protrusion 3 on the front face 24 side of the basal member 2 are each curved with a curvature. Since the entrance portion 23 to the fine hollow protrusion 3 has a curvature, the flowing of agents during delivery of the agents is facilitated. Since the base portion 34 of the fine hollow protrusion 3 has a curvature, the microneedle array 1M is less likely to break.

A ratio (R1/H1) of the radius of curvature R1 at which the base portion 34 of the fine hollow protrusion 3 on the front face 24 side of the basal member 2 is curved with a curvature, with respect to the projecting height H1 of each fine hollow protrusion 3, is preferably 0.01 or greater, and more preferably 0.02 or greater, is preferably 0.5 or less, and more preferably 0.3 or less, and, specifically, is preferably from 0.01 to 0.5, and more preferably from 0.02 to 0.3, in order to make it easier to allow agents to flow during delivery of the agents and to make the fine hollow portions less likely to break.

Furthermore, a ratio (R2/H1) of the projecting height H1 of each fine hollow protrusion 3 with respect to the radius of curvature R2 at which the entrance portion 23 to the fine hollow protrusion 3 on the back face 25 side of the basal member 2 is curved with a curvature is preferably 0.01 or greater, and more preferably 0.02 or greater, is preferably 0.4 or less, and more preferably 0.25 or less, and, specifically, is preferably from 0.01 to 0.4, and more preferably from 0.02 to 0.25, in order to make it easier to allow agents to flow during delivery of the agents and to make the fine hollow portions less likely to break.

Furthermore, it is preferable that the radius of the curvature R1 of the base portion 34 of the fine hollow protrusion 3 on the front face 24 side is smaller than the radius of the curvature R2 of the entrance portion 23 of the fine hollow protrusion 3 on the back face 25 side, in order to make the fine hollow protrusions 3 unlikely to break when inserted into the skin and to enable easy insertion of the fine hollow protrusions 3.

The opening portion 3h has an opening area S1 that is preferably 0.7 $\mu m^2$ or greater, and more preferably 20 $\mu m^2$ or greater, is preferably 200000 $\mu m^2$ or less, and more preferably 70000 $\mu m^2$ or less, and, specifically, is preferably from 0.7 to 200000 $\mu m^2$, and more preferably from 20 to 70000 $\mu m^2$, in order to make it easy to deliver agents through the microneedle array 1M.

From a similar point of view, the basal-side opening portion 2h has an opening area S2 that is preferably 0.007 $mm^2$ or greater, and more preferably 0.03 $mm^2$ or greater, is preferably 20 $mm^2$ or less, and more preferably 7 $mm^2$ or less, and, specifically, is preferably from 0.007 to 20 $mm^2$, and more preferably from 0.03 to 7 $mm^2$.

The nine fine hollow protrusions 3 arranged in an array on the upper face of the sheet-like basal member 2 are preferably such that the center-to-center distance in the longitudinal direction (Y direction) is uniform and the center-to-center distance in the lateral direction (X direction) is uniform, and, preferably, the center-to-center distance in the longitudinal direction (Y direction) is the same as the center-to-center distance in the lateral direction (X direction). Preferably, the center-to-center distance in the longitudinal direction (Y direction) between the fine hollow protrusions 3 is preferably 0.01 mm or greater, and more preferably 0.05 mm or greater, is preferably 10 mm or less, and more preferably 5 mm or less, and, specifically, is preferably from 0.01 to 10 mm, and more preferably from 0.05 to 5 mm. Furthermore, the center-to-center distance in the lateral direction (X direction) between the fine hollow protrusions 3 is preferably 0.01 mm or greater, and more preferably 0.05 mm or greater, is preferably 10 mm or less, and more preferably 5 mm or less, and, specifically, is preferably from 0.01 to 10 mm, and more preferably from 0.05 to 5 mm.

Figure 4:
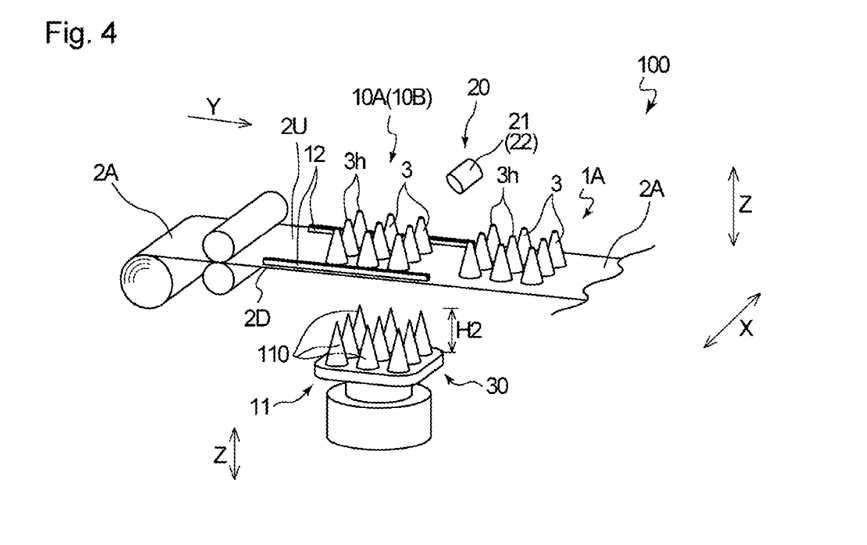
FIG. 4 is a view showing the overall configuration according to an embodiment of a manufacturing apparatus for manufacturing the fine hollow protruding tool shown in FIG. 1.
Figure 5A:
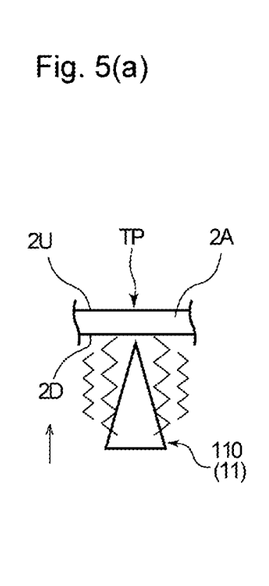

Next, a method for manufacturing the fine hollow protruding tool of the present invention will be described with reference to FIGS. 4 to 6, using a method for manufacturing the microneedle array 1M as the fine hollow protruding tool 1 described above as an example. FIG. 4 shows the overall configuration of a manufacturing apparatus 100 according to an embodiment used for implementing the manufacturing method of this embodiment. Note that, although the fine hollow protrusions 3 in the microneedle array 1M are very small as described above, for the convenience's sake, the fine hollow protrusions 3 in the microneedle array 1M are illustrated very large in FIG. 4.

The manufacturing apparatus 100 of this embodiment shown in FIG. 4 includes a protrusion precursor forming section 10A in which fine hollow protrusion precursors 3b that are hollow are formed (see FIG. 5) on the base material sheet 2A, a protrusion forming section 10B in which fine hollow protrusions 3 are formed on the base material sheet 2A, a cooling section 20, and a release section 30 that releases a later-described projecting mold part 11.

In the description below, the direction in which the base material sheet 2A is transported (the longitudinal direction of the base material sheet 2A) is taken as a Y direction, the direction that is orthogonal to the transporting direction, which is the lateral direction of the base material sheet 2A that is being transported is taken as an X direction, and the thickness direction of the base material sheet 2A that is being transported is taken as a Z direction.

As shown in FIG. 4, the protrusion precursor forming section 10A and the protrusion forming section 10B include the projecting mold part 11 that has a heating means (not shown). The projecting mold part 11 has projections 110 corresponding to the number and arrangement of fine hollow protrusions 3 of the microneedle array 1M that is to be manufactured and a schematic outer shape of each fine hollow protrusion 3, and, in the manufacturing apparatus 100 of this embodiment, nine conical projections 110 are provided corresponding to the nine truncated conical fine hollow protrusions 3. In this specification, the projecting mold part 11 is a member including the projections 110, which are portions that are inserted into the base material sheet 2A, and, in the manufacturing apparatus 100 of this embodiment, the projecting mold part 11 is arranged on a disk-like stage portion. Note that the configuration of the projecting mold part 11 is not limited to this, and it may be a projecting mold part including only the projections 110, or may be a projecting mold part 11 in which the plurality of projections 110 are arranged on a table-like support.

Furthermore, in the manufacturing apparatus 100 of this embodiment, the amount of heat that is applied by the projecting mold part 11 to the base material sheet 2A in the protrusion forming section 10B is larger than the amount of heat that is applied by the projecting mold part 11 to the base material sheet 2A in the protrusion precursor forming section 10A. Here, the amount of heat that is applied to the base material sheet 2A refers to the amount of heat that is applied to the base material sheet 2A per unit insertion height. Specifically, the condition that makes the amount of heat that is applied by the projecting mold part 11 to the base material sheet 2A in the protrusion forming section 10B larger than the amount of heat that is applied by the projecting mold part 11 to the base material sheet 2A in the protrusion precursor forming section 10A refers to satisfying at least one of the conditions: (Condition a) the insertion speed of the projecting mold part 11 into the base material sheet 2A is such that the insertion speed in the protrusion forming section 10B is slower than the insertion speed in the protrusion precursor forming section 10A; (Condition b) in the case where the heating means (not shown) of the projecting mold part 11 is an ultrasonic vibration device, the frequency of ultrasonic waves in the projecting mold part 11 of the protrusion forming section 10B is higher than the frequency of ultrasonic waves in the projecting mold part 11 of the protrusion precursor forming section 10A; (Condition c) in the case where the heating means (not shown) of the projecting mold part 11 is an ultrasonic vibration device, the amplitude of ultrasonic waves in the projecting mold part 11 of the protrusion forming section 10B is larger than the amplitude of ultrasonic waves in the projecting mold part 11 of the protrusion precursor forming section 10A; and (Condition d) in the case where the heating means (not shown) of the projecting mold part 11 is a heater device, the heater temperature of the projecting mold part 11 of the protrusion forming section 10B is higher than the heater temperature of the projecting mold part 11 of the protrusion precursor forming section 10A. In the manufacturing apparatus 100 of this embodiment, no heating means is provided other than the heating means (not shown) of the projecting mold part 11. In this specification, "no heating means is provided other than the heating means of the projecting mold part 11" refers to not only cases in which other heating means are completely excluded but also cases in which a means for heating the base material sheet 2A to a temperature lower than its softening temperature, and preferably lower than its glass transition temperature is included. Specifically, heating may be additionally performed to a temperature below the softening temperature, as long as the temperature of the base material sheet 2A reached due to heating by the heating means of the projecting mold part 11 is a temperature that is the same as or greater than the softening temperature of the base material sheet 2A. Furthermore, heating may be additionally performed to a temperature below the glass transition temperature, as long as the temperature of the base material sheet 2A reached due to heating by the heating means of the projecting mold part 11 is a temperature that is the same as or greater than the glass transition temperature and below the softening temperature. Note that it is preferable that no heating means other than the heating means provided at projecting mold parts 11A and 11B is included at all. In the manufacturing apparatus 100 of this embodiment, the heating means (not shown) of the projecting mold part 11 is an ultrasonic vibration device.

In this embodiment, first, a continuous base material sheet 2A containing a thermoplastic resin is unwound from a raw material roll of the base material sheet 2A, and is transported in the Y direction. When the base material sheet 2A has been fed to a predetermined position, transportation of the base material sheet 2A is stopped. In this manner, in this embodiment, the continuous base material sheet 2A is transported intermittently.

The base material sheet 2A is a sheet that is formed into the basal member 2 included in the microneedle array 1M that is to be manufactured, and contains a thermoplastic resin. The base material sheet 2A is preferably a sheet mainly made of thermoplastic resin, that is, containing 50% by mass or greater of thermoplastic resin, and more preferably a sheet containing 90% by mass or greater of thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Specific examples of poly-fatty acid esters include polylactic acid, polyglycolic acid, and combinations thereof. Note that the base material sheet 2A may be formed of a mixture including, for example, hyaluronic acid, collagen, starch, cellulose, etc., in addition to thermoplastic resin. The thickness of the base material sheet 2A is similar to the thickness T2 of the basal member 2 included in the microneedle array 1M that is to be manufactured.

Figure 5B:
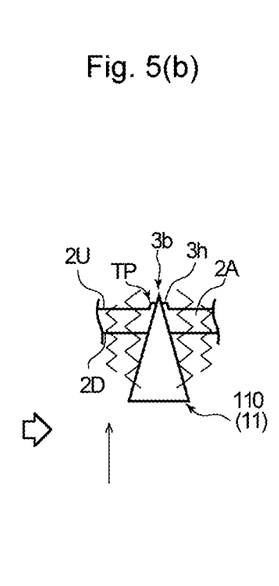
Figure 6:
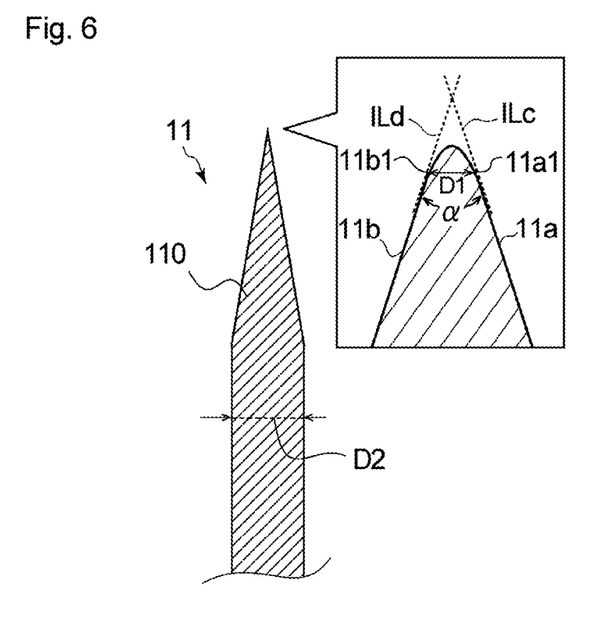
FIG. 6 is an explanatory view showing a method for measuring the tip diameter and the tip angle of a projection of a projecting mold part.

Then, in this embodiment, as shown in FIGS. 5(a) and 5(b), the projecting mold part 11 is brought into contact with one face 2D of the continuous base material sheet 2A that is being transported in the Y direction, the projecting mold part 11 is inserted into the base material sheet 2A while applying heat such that contact point TP on the base material sheet 2A soften, and thus fine hollow protrusion precursors 3b that are hollow are formed, the fine hollow protrusion precursors 3b projecting from the other face 2U of the base material sheet 2A, and respectively having opening portions 3h that penetrate through the tips on the other face 2U side of the base material sheet 2A (protrusion precursor forming step). Preferably, in the manufacturing apparatus 100 of this embodiment, nine conical projections 110 with sharp tips are arranged on the projecting mold part 11 such that the tips face upward, and the projecting mold part 11 is movable at least vertically in the thickness direction (Z direction). More preferably, in the manufacturing apparatus 100 of this embodiment, the projecting mold part 11 can be moved vertically in the thickness direction (Z direction) by an electric actuator (not shown). The operation of the projecting mold part 11 (electric actuator) is controlled by a control means (not shown) included in the manufacturing apparatus 100 of this embodiment. Note that it is preferable that the heating means (not shown) of the projecting mold part 11 is operated immediately before the projecting mold part 11 comes into contact with the base material sheet 2A to immediately before the procedure reaches a later-described cooling step.

The operation of the projecting mold part 11, and heating conditions of the heating means (not shown) included in the projecting mold part 11, such as the operation of the heating means (not shown) of the projecting mold part 11, are controlled by a control means (not shown) included in the manufacturing apparatus 100 of this embodiment.

The projections 110 of the projecting mold part 11 have an outer shape that is sharper than the outer shape of the fine hollow protrusions 3 included in the microneedle array 1M. The projections 110 of the projecting mold part 11 each have a height H2 (see FIG. 4) that is higher than the height H1 of the microneedle array 1M that is to be manufactured, and it is preferably 0.01 mm or greater, and more preferably 0.02 mm or greater, is preferably 30 mm or less, and more preferably 20 mm or less, and, specifically, is preferably from 0.01 to 30 mm, and more preferably from 0.02 to 20 mm.

The projections 110 of the projecting mold part 11 each have a tip diameter D1 (see FIG. 6) that is preferably 0.001 mm or greater, and more preferably 0.005 mm or greater, is preferably 1 mm or less, and more preferably 0.5 mm or less, and, specifically, is preferably from 0.001 to 1 mm, and more preferably from 0.005 to 0.5 mm. The tip diameter D1 of the projections 110 of the projecting mold part 11 is measured as follows.

The projections 110 of the projecting mold part 11 each have a base diameter D2 (see FIG. 6) that is preferably 0.1 mm or greater, and more preferably 0.2 mm or greater, is preferably 5 mm or less, and more preferably 3 mm or less, and, specifically, is preferably from 0.1 to 5 mm, and more preferably from 0.2 to 3 mm.

The projections 110 of the projecting mold part 11 each have a tip angle α (see FIG. 6) that is preferably 1 degree or greater, and more preferably 5 degrees or greater, in order to facilitate making the projections 110 sufficiently strong. Furthermore, in order to obtain fine hollow protrusions 3 with an appropriate angle, the tip angle α is preferably 60 degrees or less, and more preferably 45 degrees or less, and, specifically, is preferably from 1 to 60 degrees, and more preferably from 5 to 45 degrees. The tip angle α of the projections 110 of the projecting mold part 11 is measured as follows.

Measurement of Tip Diameter of Projections 110 of Projecting Mold Part 11

The tip portion of a projection 110 of the projecting mold part 11 is observed in a state of being enlarged at a predetermined magnification using a scanning electron microscope (SEM) or a microscope. Next, as shown in FIG. 6, an imaginary straight line ILc is extended along the straight-line portion of one lateral side 11a of two lateral sides 11a and 11 b, and an imaginary straight line ILd is extended along the straight-line portion the other lateral side 11b. Then, a point where the lateral side 11a separates from the imaginary straight line ILc on the tip side is obtained as a first tip point 11a1, and a point where the other lateral side 11b separates from the imaginary straight line ILd is obtained as a second tip point 11b1. A length D1 of a straight line that links the thus obtained first tip point 11a1 and second tip point 11b1 is measured using a scanning electron microscope (SEM), and the measured length of the straight line is taken as the tip diameter of the projections 110.

Measurement of Tip Angle α of Projections 110 of Projecting Mold Part 11

The tip portion of a projection 110 of the projecting mold part 11 is observed in a state of being enlarged at a predetermined magnification using a scanning electron microscope (SEM) or a microscope. Next, as shown in FIG. 6, an imaginary straight line ILc is extended along the straight-line portion of one lateral side 11a of two lateral sides 11a and 11 b, and an imaginary straight line ILd is extended along the straight-line portion the other lateral side 11b. An angle formed by the imaginary straight line ILc and the imaginary straight line ILd is measured using a scanning electron microscope (SEM), and the measured angle is taken as the tip angle α of the projections 110 of the projecting mold part 11.

The projecting mold part 11 is made of a high-strength material that is unlikely to break. Examples of the material for the projecting mold part 11 include metals, such as steel, stainless steel, aluminum, an aluminum alloy, nickel, a nickel alloy, cobalt, a cobalt alloy, copper, a copper alloy, beryllium copper, and a beryllium copper alloy, and ceramics.

The protrusion precursor forming section 10A in the manufacturing apparatus 100 of this embodiment includes supports 12 that support the base material sheet 2A while the projecting mold part 11 is inserted into the base material sheet 2A, as shown in FIG. 4. The supports 12 are arranged on the other face 2U side of the base material sheet 2A, and serve to make the base material sheet 2A less likely to warp when the projecting mold part 11 is inserted from the one face 2D. Accordingly, the supports 12 are arranged in a portion of the base material sheet 2A other than the region into which the projecting mold part 11 is inserted, and, in the manufacturing apparatus 100 of this embodiment, are constituted by a pair of plate-like members that are arranged on both sides along the transporting direction of the base material sheet 2A (Y direction) so as to extend parallel to the transporting direction (Y direction). Each of the supports 12 are arranged throughout the protrusion precursor forming section 10A, the protrusion forming section 10B, the cooling section 20, and the release section 30.

The material for forming the supports 12 may be the same as the material for forming the projecting mold part 11, and examples thereof include a synthetic resin and the like.

In the protrusion precursor forming step of this embodiment, as shown in FIG. 4, the pair of supports 12, 12 arranged on the other face 2U side of the continuous base material sheet 2A that has been unwound from the raw material roll and is being transported in the Y direction support both sides along the transporting direction of the base material sheet 2A (Y direction). Then, the tip portions of the projections 110 of the projecting mold part 11 are brought into contact with the one face 2D (the lower face) of the portion of the base material sheet 2A not supported by the supports 12, 12, that is, the middle region of the base material sheet 2A between the pair of supports 12, 12. In this manner, in the protrusion precursor forming step, the other face 2U (the upper face) corresponding to the contact points TP of the base material sheet 2A with which the projections 110 of the projecting mold part 11 have been brought into contact is not provided with, for example, depressions that are to be fitted to the projecting mold part 11 for forming protrusions, and are not held down.

In this embodiment, as shown in FIG. 5(a), the ultrasonic vibration device causes the projecting mold part 11 to vibrate ultrasonically at the contact points TP, and thus the contact points TP are softened by heat generated through friction at the contact points TP. Then, in the protrusion precursor forming step of this embodiment, while the contact points TP are softened, as shown in FIG. 5(b), the projecting mold part 11 is raised from the one face 2D (the lower face) of the base material sheet 2A toward the other face 2U (the upper face), and the tip portions of the projections 110 are inserted into the base material sheet 2A, so that fine hollow protrusion precursors 3b that are hollow are formed, the fine hollow protrusion precursors 3b projecting from the other face 2U (the upper face) of the base material sheet 2A, and respectively having opening portions 3h that penetrate through the base material sheet 2A.

In the protrusion precursor forming step of this embodiment, ultrasonic vibrations generated by the ultrasonic vibration device of the projecting mold part 11 are such that the vibration frequency thereof (hereinafter, referred to as "frequency") is preferably 10 kHz or greater, and more preferably 15 kHz or greater, is preferably 50 kHz or less, and more preferably 40 kHz or less, and, specifically, is preferably from 10 to 50 kHz, and more preferably from 15 to 40 kHz, in order to form the fine hollow protrusion precursors 3b having the opening portions 3h with ease.

Furthermore, ultrasonic vibrations generated by the ultrasonic vibration device of the projecting mold part 11 are such that the amplitude thereof is preferably 1 μm or greater, and more preferably 5 μm or greater, is preferably 60 μm or less, and more preferably 50 μm or less, and, specifically, is preferably from 1 to 60 μm, and more preferably from 5 to 50 μm, in order to form the fine hollow protrusion precursors 3b having the opening portions 3h with ease. In the case where an ultrasonic vibration device is used as in this embodiment, in the protrusion precursor forming step, the frequency and the amplitude of ultrasonic vibrations of the projecting mold part 11 may be adjusted within the above-described range.

In the protrusion precursor forming step of this embodiment, if the insertion speed at which the projecting mold part 11 is inserted into the base material sheet 2A is too slow, the resin is softened excessively, and the size of the opening portions 3h increases too much, whereas, if the insertion speed is too fast, softening is insufficient, and the opening portions 3h will not be formed. Thus, in order to efficiently form the fine hollow protrusion precursors 3b having the opening portions 3h, the insertion speed is preferably 0.1 mm/sec or greater, and more preferably 1 mm/sec or greater, is preferably 1000 mm/sec or less, and more preferably 800 mm/sec or less, and, specifically, is preferably from 0.1 to 1000 mm/sec, and more preferably from 1 to 800 mm/sec.

In the protrusion precursor forming step of this embodiment, the insertion height by which the projecting mold part 11 is inserted into the base material sheet 2A is preferably 0.001 mm or greater, and more preferably 0.01 mm or greater, is preferably 2 mm or less, and more preferably 1 mm or less, and, specifically, is preferably from 0.001 to 2 mm, and more preferably from 0.01 to 1 mm, in order to efficiently form the fine hollow protrusion precursors 3b having the opening portions 3h. Here, "insertion height" refers to the distance between the apex of a projection 110 of the projecting mold part 11 and the other face 2U of the base material sheet 2A in a state where the projection 110 of the projecting mold part 11 is inserted into the base material sheet 2A. Accordingly, the insertion height in the protrusion precursor forming step refers to the distance from the other face 2U to the apex of a projection 110 as measured in the perpendicular direction in a state where the projection 110 has been inserted to the deepest position and has emerged from the other face 2U of the base material sheet 2A in the protrusion precursor forming step.

Next, in the manufacturing apparatus 100 of this embodiment, as shown in FIG. 4, the protrusion forming section 10B is installed on the path downstream of the protrusion precursor forming section 10A. In this embodiment, after the protrusion precursor forming step, in a state where the projecting mold part 11 has been inserted into the fine hollow protrusion precursors 3b, the projecting mold part 11 is further inserted into the base material sheet 2A while applying heat such that the contact points TP on the base material sheet 2A soften, so that fine hollow protrusions 3 projecting from the other face 2U of the base material sheet 2A by a longer distance are formed (fine hollow protrusion forming step). Preferably, in the manufacturing apparatus 100 of this embodiment, the projecting mold part 11 is further moved upward in the thickness direction (Z direction) by an electric actuator (not shown), and the ultrasonic vibration device causes the projecting mold part 11 to vibrate ultrasonically at the contact points TP on the base material sheet 2A in a state where the projections 110 of the projecting mold part 11 have been inserted into the fine hollow protrusion precursors 3b, and thus the contact points TP are further softened by heat generated through friction. In this state, the projections 110 of the projecting mold part 11 are further inserted into the base material sheet 2A, so that fine hollow protrusions 3 further projecting from the other face 2U of the base material sheet 2A are formed. Note that, in the fine hollow protrusion forming step of this embodiment, as shown in FIG. 4, the pair of supports 12, 12 arranged on the other face 2U side (the upper face) of the continuous base material sheet 2A support both sides along the transporting direction of the base material sheet 2A (Y direction).

Figure 5C:
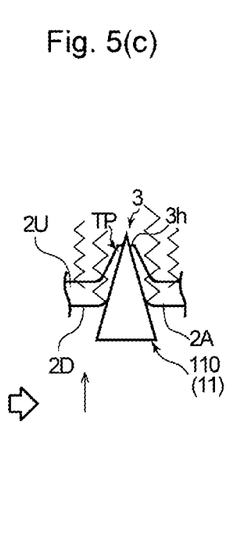

In the fine hollow protrusion forming step of this embodiment, as shown in FIG. 5(c), the frequency and the amplitude of ultrasonic vibrations of the projecting mold part 11 generated by the ultrasonic vibration device are respectively the same as the frequency and the amplitude of ultrasonic vibrations in the protrusion precursor forming step. Note that the opening area of the opening portion 3h of each fine hollow protrusion 3 formed in the fine hollow protrusion forming step is the same as or greater than the opening area S1 of the opening portion 3h of each fine hollow protrusion precursor 3b formed in the protrusion precursor forming step, but is preferably the same as the opening area S1.

In the fine hollow protrusion forming step of this embodiment, the insertion speed at which the projecting mold part 11 is inserted into the base material sheet 2A is slower than the insertion speed at which the projecting mold part 11 is inserted into the base material sheet 2A in the protrusion precursor forming step. In the fine hollow protrusion forming step of this embodiment, if the insertion speed at which the projecting mold part 11 is inserted into the base material sheet 2A is too slow, the resin is softened excessively, and the size of the opening portions 3h changes too significantly, whereas, if the insertion speed is too fast, softening is insufficient, and the height of the fine hollow protrusions 3 is likely to be insufficient. Thus, in order to efficiently form the fine hollow protrusions 3 having the opening portions 3h, the insertion speed is preferably 0.1 mm/sec or greater, and more preferably 1 mm/sec or greater, is preferably 1000 mm/sec or less, and more preferably 800 mm/sec or less, and, specifically, is preferably from 0.1 to 1000 mm/sec, and more preferably from 1 to 800 mm/sec.

In the fine hollow protrusion forming step of this embodiment, after the fine hollow protrusion precursors $3b$ having the opening portions $3h$ are formed in the protrusion precursor forming step, raising of the projecting mold part 11 decelerates at a constant rate, and raising of the projecting mold part 11 in a heated state is stopped. Since raising of the projecting mold part 11 decelerates at a constant rate in this manner, it is easy to manufacture a microneedle array 1M having the fine hollow protrusions 3 in which the wall thickness T1 in the apex-side region TB is thinner than the wall thickness T2 in the lower-side region BP, and the gap M1 between the inner walls 31, 31 in the apex-side region TB is smaller than the gap M2 between the inner walls 31, 31 in the lower-side region BP. Furthermore, at this time, the entrance portions of the fine hollow protrusions 3 on the one face 2D side of the base material sheet 2A and the base portions of the fine hollow protrusions 3 on the other face 2U side of the base material sheet 2A are curved with a curvature.

In the fine hollow protrusion forming step of this embodiment, if the softening time that is the time from when raising of the projecting mold part 11 in a heated state is stopped until when a cooling step, which is the next step, is performed while keeping the projections 110 of the projecting mold part 11 inserted in the fine hollow protrusions 3 is too long, the contact points TP on the base material sheet 2A are excessively softened, but, in order to compensate for insufficient softening, the softening time is preferably 0 seconds or greater, and more preferably 0.1 seconds or greater, is preferably 10 seconds or less, and more preferably 5 seconds or less, and, specifically, is preferably from 0 to 10 seconds, and more preferably from 0.1 to 5 seconds.

In the fine hollow protrusion forming step of this embodiment, the insertion height by which the projecting mold part 11 is inserted into the base material sheet 2A is preferably 0.01 mm or greater, and more preferably 0.02 mm or greater, is preferably 10 mm or less, and more preferably 5 mm or less, and, specifically, is preferably from 0.01 to 10 mm, and more preferably from 0.02 to 5 mm, in order to efficiently form the fine hollow protrusions 3 having the opening portions $3h$.

In this embodiment, the conditions of the heating means (not shown) included in the projecting mold part 11 in the protrusion precursor forming step are the same as the conditions of the heating means (not shown) included in the projecting mold part 11 in the fine hollow protrusion forming step, and the speed at which the projecting mold part 11 is further inserted into the base material sheet 2A in the fine hollow protrusion forming step is slower than the speed at which the projecting mold part 11 is inserted into the base material sheet 2A in the protrusion precursor forming step. Specifically, the manufacturing apparatus 100 of this embodiment is one in which the heating means (not shown) of the projecting mold part 11 is an ultrasonic vibration device, wherein the frequency and the amplitude of ultrasonic vibrations of the projecting mold part 11 included in the protrusion forming section 10B are the same as the frequency and the amplitude of ultrasonic vibrations of the projecting mold part 11 included in the protrusion precursor forming section 10A, that is, the conditions (b) and (c) described above are not satisfied. However, in this embodiment, the insertion speed of inserting the projecting mold part 11 into the base material sheet 2A is such that the insertion speed in the fine hollow protrusion forming step is slower than the insertion speed in the protrusion precursor forming step, that is, the condition (a) described above is satisfied. Thus, the amount of heat that is applied by the projecting mold part 11 to the base material sheet 2A in the fine hollow protrusion forming step is larger than the amount of heat that is applied by the projecting mold part 11 to the base material sheet 2A in the protrusion precursor forming step.

Furthermore, in the manufacturing apparatus 100 of this embodiment, the insertion speed of inserting the projecting mold part 11 into the base material sheet 2A is such that the insertion speed is continuously lowered from the protrusion precursor forming step to the fine hollow protrusion forming step. That is to say, the insertion speed is gradually reduced, so that raising of the projecting mold part 11 decelerates at a constant rate. Thus, in this embodiment, the amount of heat per unit insertion height that is applied by the projecting mold part 11 to the base material sheet 2A in the protrusion precursor forming step and the amount of heat per unit insertion height that is applied by the projecting mold part 11 to the base material sheet 2A in the fine hollow protrusion forming step continuously change from the latter part of the protrusion precursor forming step to the early part of the fine hollow protrusion forming step. Note that "amount of heat per unit insertion height" refers to a value obtained by dividing the total amount of heat applied to the base material sheet 2A, by the movement distance of the projecting mold part 11. For example, in the protrusion precursor forming step, it is a value obtained by dividing the total amount of heat applied to the base material sheet 2A from when the projecting mold part 11 is brought into contact with the base material sheet 2A to when this step is completed, by the total movement distance in the step.

Figure 5D:
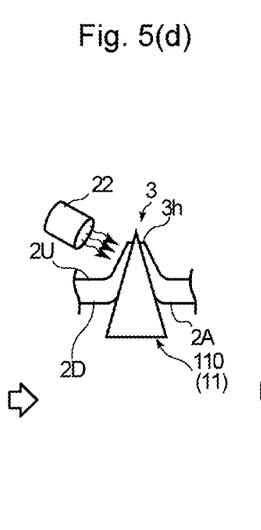

Next, in the manufacturing apparatus 100 of this embodiment, as shown in FIG. 4, the cooling section 20 is installed on the path downstream of the protrusion forming section 10B. As shown in FIG. 4, the cooling section 20 includes a cold air blowing device 21. In this embodiment, after the fine hollow protrusion forming step, the fine hollow protrusions 3 are cooled by using the cold air blowing device 21 in a state where the projecting mold part 11 is inserted in the fine hollow protrusions 3 (cooling step). In the manufacturing apparatus 100 of this embodiment, the cold air blowing device 21 is provided with an air vent 22 for blowing cold air (see FIG. 5($d$)) onto the other face 2U side (the upper face side) of the base material sheet 2A, and the fine hollow protrusions 3 are cooled by cold air blown from the air vent 22. Note that a configuration is also possible in which the cold air blowing device has a hollow shape that covers the entire other face 2U side (the upper face side) and the entire one face 2D side (the lower face side) of the continuous base material sheet 2A that is being transported, and the continuous base material sheet 2A is transported in the transporting direction (Y direction) through the cold air blowing device, wherein the air vent 22 for blowing cold air is provided, for example, in a hollow portion. The cooling temperature and the cooling time of the cold air blowing device 21 are controlled by a control means (not shown) included in the manufacturing apparatus 100 of this embodiment.

In the cooling step of this embodiment, as shown in FIG. 5($d$), cooling is performed while keeping the projections 110 of the projecting mold part 11 inserted in the fine hollow protrusions 3 by blowing cold air from the air vent 22 arranged on the other face 2U side (the upper face side) of the base material sheet 2A in a state where the projections 110 of the projecting mold part 11 are inserted in the fine hollow protrusions 3. Note that, when performing cooling, generation of ultrasonic vibrations by the ultrasonic vibration device of the projecting mold part 11 may be continued or stopped, but, in order to keep the shape of the fine hollow protrusions 3 constant without it excessively changing, the generation of ultrasonic vibrations is preferably stopped.

The temperature of the cold air to be blown is preferably −50° C. or greater, and more preferably −40° C. or greater, is preferably 26° C. or less, and more preferably 10° C. or less, and, specifically, is preferably from −50 to 26° C., and more preferably from −40 to 10° C., in order to form the fine hollow protrusions 3 having the opening portions 3h.

The cooling time for cooling by blowing cold air is preferably 0.01 seconds or greater, and more preferably 0.5 seconds or greater, is preferably 60 seconds or less, and more preferably 30 seconds or less, and, specifically, is preferably from 0.01 to 60 seconds, and more preferably from 0.5 to 30 seconds, in order to balance moldability and processing time.

Figure 5E:
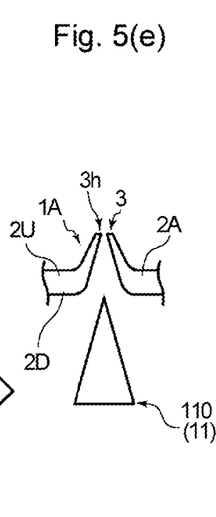

Next, in the manufacturing apparatus 100 of this embodiment, as shown in FIG. 4, the release section 30 is installed on the path downstream of the cooling section 20. In this embodiment, after the cooling step, the projecting mold part 11 is released from the interior of the fine hollow protrusions 3, so that a precursor 1A of the microneedle arrays 1M is formed (release step). Specifically, in the release step of this embodiment, as shown in FIG. 5(e), the projecting mold part 11 is lowered from the one face 2D (the lower face) of the base material sheet 2A, and the projections 110 of the projecting mold part 11 are released from the state in which the projections 110 of the projecting mold part 11 are inserted in the fine hollow protrusions 3, so that a precursor 1A of a continuous fine hollow protruding tool is formed, the continuous fine hollow protruding tool being formed into the microneedle arrays 1M, in each of which the fine hollow protrusions 3 are arranged in an array respectively having the opening portions 3h and respectively having hollow interiors.

The thus formed precursor 1A of the microneedle arrays 1M is then transported downstream in the transporting direction (Y direction). Then, the precursor 1A is cut in a predetermined range in a cutting step, and thus a microneedle array 1M can be manufactured as the fine hollow protruding tool 1 of the first embodiment including a sheet-like basal member 2 and a plurality of fine hollow protrusions 3 as shown in FIG. 1. Fine hollow protruding tools 1 can be continuously and efficiently manufactured on the other face 2U side (the upper face side) of the base material sheet 2A, by repeating the above-described steps.

The microneedle array 1M manufactured as described above may be further shaped into a predetermined shape in subsequent steps, or the shape of the base material sheet 2A may be adjusted in advance into a desired shape before the step of inserting the projecting mold part 11.

As described above, according to the manufacturing method of this embodiment for manufacturing the microneedle array 1M using the manufacturing apparatus 100, it is possible to precisely manufacture a microneedle array 1M having the fine hollow protrusions 3 in which the wall thickness T1 in the apex-side region TB is thinner than the wall thickness T2 in the lower-side region BP, and the gap M1 between the inner walls 31, 31 in the apex-side region TB is smaller than the gap M2 between the inner walls 31, 31 in the lower-side region BP.

Figure 7:
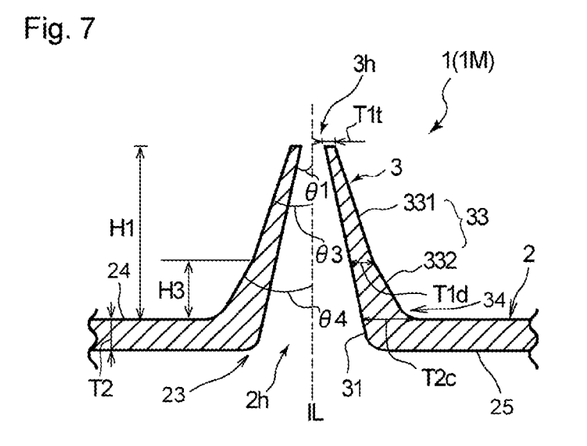
FIG. 7 is a vertical cross-sectional view passing through an apex of a fine hollow protrusion of a fine hollow protruding tool according to a second embodiment of a fine hollow protruding tool having opening portions of the present invention (view corresponding to FIG. 3).

Next, the fine hollow protruding tool of the present invention will be described with reference to FIG. 7 based on a fine hollow protruding tool 1 according to a second embodiment. FIG. 7 shows a cross-sectional view of the microneedle array 1M as the fine hollow protruding tool 1 of the second embodiment. In this description, aspects different from those in the foregoing first embodiment will be mainly described.

While in the foregoing first embodiment, the outer wall 32 of the fine hollow protrusion 3 in the microneedle array 1M is formed in the shape of a straight line, in the microneedle array 1M of the second embodiment, a step is provided on the outer wall 33 of the fine hollow protrusion 3.

In the second embodiment, the microneedle array 1M is such that, in any vertical cross-section passing through the apex of a fine hollow protrusion 3 as shown in FIG. 7, an angle formed by the perpendicular line IL passing through the apex of the fine hollow protrusion 3 and the outer wall 33 of the fine hollow protrusion 3 on the apex portion side is different from that on the basal member side. Specifically, the outer wall 33 of the fine hollow protrusion 3 in the microneedle array 1M of the second embodiment has a two-step structure consisting of an apex portion-side outer wall 331 located on the apex portion side and formed in the shape of a straight line, and a basal member-side outer wall 332 located on the basal member side and formed in the shape of a straight line with a degree of inclination different from that of the apex portion-side outer wall 331, and an angle θ4 formed between the perpendicular line IL and the basal member-side outer wall 332 is larger than an angle θ3 formed between the perpendicular line IL and the apex portion-side outer wall 331. That is to say, the fine hollow protrusions 3 in the microneedle array 1M of the second embodiment are each such that the inner wall 31 is formed in the shape of a straight line, whereas the outer wall 33 is provided with a step. If the fine hollow protrusions 3 are formed in this manner, it is possible to make the wall thickness on the basal member side larger than that on the apex portion side, and to make the wall thickness on the basal member side even larger toward the base. Accordingly, it is possible to make the fine hollow protrusions 3 less likely to break.

In order to reduce pain when piercing the skin with the fine hollow protrusions 3 and to make the fine hollow protrusions 3 unlikely to break, a ratio (θ3/θ4) of the angle θ3 formed between the perpendicular line IL and the apex portion-side outer wall 331 with respect to the angle θ4 formed between the perpendicular line IL and the basal member-side outer wall 332 is preferably 0.05 or greater, and more preferably 0.1 or greater, is preferably 0.6 or less, and more preferably 0.5 or less, and, specifically, is preferably from 0.05 to 0.6, and more preferably from 0.1 to 0.5.

Furthermore, in order to reduce pain when piercing the skin with the fine hollow protrusions 3 and to make the fine hollow protrusions 3 unlikely to break, a ratio (H3/H1) of the height H3 from the upper face of the basal member 2 to the step with respect to the projecting height H1 of the microneedle array 1M is preferably 0.05 or greater, and more preferably 0.1 or greater, is preferably 0.05 or less, and more preferably 0.6 or less, and, specifically, is preferably from 0.05 to 0.6, and more preferably from 0.1 to 0.5.

The fine hollow protrusions 3 in the microneedle array 1M of the second embodiment each have a wall thickness T1d at the step that is preferably 0.005 mm or greater, and more preferably 0.01 mm or greater, is preferably 0.5 mm or less, and more preferably 0.3 mm or less, and, specifically, is preferably from 0.005 to 0.5 mm, and more preferably from 0.01 to 0.3 mm, in order to reduce pain when piercing the skin and to make the fine hollow protrusions 3 unlikely to break.

The fine hollow protrusions 3 in the microneedle array 1M of the second embodiment each have a wall thickness T2c on the upper face of the basal member 2 that is preferably 0.02 mm or greater, and more preferably 0.01 mm or greater, is preferably 0.8 mm or less, and more preferably 0.5 mm or less, and, specifically, is preferably from 0.01 to 0.8 mm, and more preferably from 0.02 to 0.5 mm, in order to reduce pain when piercing the skin and to make the fine hollow protrusions 3 unlikely to break.

Note that, although the second embodiment has been described using a configuration in which the outer wall 33 of each fine hollow protrusion 3 is provided with one step, the outer wall 33 may be provided with two or more steps. That is to say, the inclination angle of the outer wall 33 may be increased in a stepwise manner from the apex portion side toward the basal member side. For example, another outer wall whose inclination angle is larger than that of the apex portion-side outer wall 331 and smaller than that of the basal member-side outer wall 332 may be provided between the apex portion-side outer wall 331 and the basal member-side outer wall 332.

Furthermore, in the microneedle array 1M of the second embodiment, in the fine hollow protrusion forming step in the manufacturing method according to the first embodiment, the projecting mold part 11 is further inserted into the base material sheet 2A while applying heat such that the base material sheet 2A softens in a state where the projecting mold part 11 has been inserted into the fine hollow protrusion precursors 3b, so that portions of the apex portion-side outer walls 331 are formed. Then, the portions of the basal member-side outer walls 332 can be formed by further inserting the projecting mold part 11 into the base material sheet 2A while applying heat in an amount lower than that applied when forming the portions of the apex portion-side outer walls 331. In this manner, after the portions of the apex portion-side outer walls 331 have been formed, the projecting mold part 11 is stopped once, and then the projecting mold part 11 is moved at an insertion speed slower than that applied when forming the portions of the apex portion-side outer walls 331 while maintaining the same frequency and amplitude of ultrasonic vibrations, so that the portions of the basal member-side outer walls 332 are formed. That is to say, after the portions of the apex portion-side outer walls 331 have been formed, the portions of the basal member-side outer walls 332 are formed.

Above, the fine hollow protruding tool of the present invention has been described based on the microneedle array 1M according to a preferable embodiment, but the present invention is not limited to the foregoing embodiments, and may be changed as appropriate.

For example, although the microneedle array 1M as the fine hollow protruding tool 1 according to the foregoing embodiments is such that nine truncated conical fine hollow protrusions 3 are arranged in an array on the upper face of the sheet-like basal member 2, it is also possible that the microneedle array 1M has one fine hollow protrusion 3. Furthermore, although the microneedle array 1M as the fine hollow protruding tool 1 according to the foregoing embodiments is such that the opening portion 3h located at the tip of each fine hollow protrusion 3 is concentric with the basal-side opening portion 2h located in the lower face, they do not have to be concentric with each other. That is to say, the opening portions 3h of the fine hollow protruding tool 1 do not have to be located at the tips as long as they are located on the tip side of the fine hollow protrusions 3.

Furthermore, although the method for manufacturing the microneedle array 1M according to the foregoing embodiments was described using an ultrasonic vibration device as the heating means of the projecting mold part 11, the heating means of the projecting mold part 11 may also be a heater device.

If the heating means of the projecting mold part 11 is a heater device, the heater device heats the projecting mold part 11 at the contact points TP, and thus the contact points TP are softened by the heat generated at the contact points TP. Then, in the protrusion precursor forming step, while the contact points TP are softened, the projecting mold part 11 is raised from the one face 2D (the lower face) of the base material sheet 2A toward the other face 2U (the upper face), and the tip portions of the projections 110 are inserted into the base material sheet 2A, so that fine hollow protrusion precursors 3b that are hollow are formed, the fine hollow protrusion precursors 3b projecting from the other face 2U (the upper face) of the base material sheet 2A, and respectively having opening portions 3h that penetrate through the base material sheet 2A. The heating temperature of the base material sheet 2A due to the projecting mold part 11 is preferably a temperature that is the same as or greater than the glass transition temperature (Tg) of the base material sheet 2A used and that is below the melting temperature thereof, and more preferably a temperature that is the same as or greater than the softening temperature of the resin and that is below the melting temperature thereof, in order to form the fine hollow protrusion precursors 3b. In the fine hollow protrusion forming step, the heater device heats the projecting mold part 11 at the contact points TP at the same temperature as that in the protrusion precursor forming step, and, while the contact points TP are softened by the heat generated at the contact points TP, the projecting mold part 11 is further raised from the one face 2D (the lower face) of the base material sheet 2A toward the other face 2U (the upper face), and the tip portions of the projections 110 are further inserted into the base material sheet 2A, so that fine hollow protrusions 3 projecting by a longer distance from the other face 2U (the upper face) of the base material sheet 2A and having the opening portions 3h are formed. Note that, in the fine hollow protrusion forming step, the insertion speed at which the projecting mold part 11 is inserted into the base material sheet 2A is slower than the insertion speed at which the projecting mold part 11 is inserted into the base material sheet 2A in the protrusion precursor forming step.

Furthermore, for example, in the method for manufacturing the microneedle array 1M according to the foregoing embodiments, the frequency and the amplitude of ultrasonic vibrations of the projecting mold part 11 included in the protrusion forming section 10B are the same as the frequency and the amplitude of ultrasonic vibrations of the projecting mold part 11 included in the protrusion precursor forming section 10A, that is, (Condition b) and (Condition c) described above are not satisfied. However, the insertion speed in the fine hollow protrusion forming step is slower than the insertion speed in the protrusion precursor forming step, and thus (Condition a) described above is satisfied. As a result, the amount of heat that is applied by the projecting mold part 11 to the base material sheet 2A in the fine hollow protrusion forming step is larger than the amount of heat that is applied by the projecting mold part 11 to the base material sheet 2A in the protrusion precursor forming step.

That is to say, the method for manufacturing the microneedle array 1M according to the foregoing embodiments is a manufacturing method in which the conditions of the heating means included in the projecting mold part 11 in the protrusion precursor forming step are the same as the conditions of the heating means included in the projecting mold part 11 in the fine hollow protrusion forming step, and the speed at which the projecting mold part 11 is further inserted into the base material sheet 2A in the fine hollow protrusion forming step is slower than the speed at which the projecting mold part 11 is inserted into the base material sheet 2A in the protrusion precursor forming step. However, a manufacturing method may be employed in which the speed at which the projecting mold part 11 is inserted into the base material sheet 2A in the protrusion precursor forming step is the same as the speed at which the projecting mold part 11 is further inserted into the base material sheet 2A in the fine hollow protrusion forming step, and the amount of heat that is applied to the base material sheet 2A in the conditions of the heating means included in the projecting mold part 11 in the fine hollow protrusion forming step is larger than the amount of heat that is applied to the base material sheet 2A in the conditions of the heating means included in the projecting mold part 11 in the protrusion precursor forming step. Specifically, it is also possible that, although (Condition a) described above is not satisfied, the frequency or the amplitude of ultrasonic vibrations of the projecting mold part 11 included in the protrusion forming section 10B is larger than the frequency or the amplitude of ultrasonic vibrations of the projecting mold part 11 included in the protrusion precursor forming section 10A, that is, (Condition b) or (Condition c) described above is satisfied, as a result of which, the amount of heat that is applied by the projecting mold part 11 to the base material sheet 2A in the fine hollow protrusion forming step is larger than the amount of heat that is applied by the projecting mold part 11 to the base material sheet 2A in the protrusion precursor forming step.

In a similar manner, in the manufacturing apparatus according to the foregoing embodiments in which the heating means of the projecting mold part 11 is a heater device, when the heater temperature of the projecting mold part 11 of the protrusion forming section 10B is the same as the heater temperature of the projecting mold part 11 of the protrusion precursor forming section 10A, (Condition d) described above is not satisfied, but, if the insertion speed in the fine hollow protrusion forming step is slower than the insertion speed in the protrusion precursor forming step, (Condition a) described above is satisfied. As a result, the amount of heat that is applied by the projecting mold part 11 to the base material sheet 2A in the fine hollow protrusion forming step is larger than the amount of heat that is applied by the projecting mold part 11 to the base material sheet 2A in the protrusion precursor forming step. Furthermore, it is also possible that, although (Condition a) described above is not satisfied, the heater temperature of the projecting mold part 11 of the protrusion forming section 10B is higher than the heater temperature of the projecting mold part 11 of the protrusion precursor forming section 10A, that is, (Condition d) described above is satisfied, as a result of which, the amount of heat that is applied by the projecting mold part 11 to the base material sheet 2A in the fine hollow protrusion forming step is larger than the amount of heat that is applied by the projecting mold part 11 to the base material sheet 2A in the protrusion precursor forming step. Furthermore, all of (Condition a), (Condition b), (Condition c), and (Condition d) described above may be satisfied.

Furthermore, in the method for manufacturing the microneedle array 1M according to the foregoing embodiments, the projecting mold part 11 can be moved vertically in the thickness direction (Z direction) by an electric actuator (not shown), but it is also possible to use a projecting mold part 11 of a box-motion type that follow an endless track.

Furthermore, in the method for manufacturing the microneedle array 1M according to the foregoing embodiments, as shown in FIG. 4, the projecting mold part 11 is inserted upward from the lower side relative to the base material sheet 2A, but the positional relationship of the projecting mold part or the support relative to the base material sheet, and the insertion direction are not limited thereto, and it is also possible to mold the microneedle array 1M downward from the upper side.

The following fine hollow protruding tools will be further described below with respect to the foregoing embodiments of the present invention.

<1> A fine hollow protruding tool comprising a basal member and a fine hollow protrusion which project from the basal member, the fine hollow protrusion having an opening portion on a tip side thereof and an interior space formed to link to the opening portion,
wherein, in any vertical cross-section passing through an apex of the fine hollow protrusion,
a wall thickness in an apex-side region on the apex side is thinner than a wall thickness in a lower-side region that is closer to the basal member than the apex-side region, and a gap between inner walls in the apex-side region is smaller than a gap between the inner walls in the lower-side region, a base portion of the fine hollow protrusion projecting from the basal member has a curvature, and
an entrance portion to the fine hollow protrusion, on an opposite face of the basal member opposite from a face from which the fine hollow protrusion projects, has a curvature.

<2> The fine hollow protruding tool as set forth in the clause <1>, wherein the wall thickness in the apex-side region is uniform around the entire circumference.

<3> The fine hollow protruding tool as set forth in the clause <1> or <2>, wherein, in any vertical cross-section passing through an apex of the fine hollow protrusion, an angle θ2 formed by a perpendicular line passing through the apex and an outer wall of the fine hollow protrusion is larger than an angle θ1 formed by the perpendicular line and an inner wall of the fine hollow protrusion.

<4> The fine hollow protruding tool as set forth in the clause <3>, wherein the interior space and an outer shape of the fine hollow protrusion are each formed in a truncated conical shape, and, in any vertical cross-section passing through the apex of the fine hollow protrusion, the angle formed by the perpendicular line passing through the apex and the outer wall is larger than the angle formed by the perpendicular line and the inner wall.

<5> The fine hollow protruding tool as set forth in the clause <3> or <4>, wherein a ratio (θ2/θ1) of the angle θ2 formed by the perpendicular line passing through the apex and the outer wall with respect to the angle θ1 formed by the perpendicular line passing through the apex and the inner wall is preferably from 0.03 to 90 inclusive, and more preferably from 0.1 to 45.

<6> The fine hollow protruding tool as set forth in any one of the clauses <3> to <5>, wherein the angle θ1 formed by the perpendicular line passing through the apex and the inner wall is preferably from 0.5 to 30 degrees inclusive, and more preferably from 2.5 to 22.5 degrees.

<7> The fine hollow protruding tool as set forth in any one of the clauses <3> to <6>, wherein the angle θ2 formed by the perpendicular line passing through the apex and the outer wall is preferably from 1 to 45 degrees inclusive, and more preferably from 3 to 30 degrees.

<8> The fine hollow protruding tool as set forth in any one of the clauses <1> to <7>, wherein, in any vertical cross-section passing through an apex of the fine hollow protrusion, a perpendicular line passing through the apex passes through an apex-side center position at which a gap between the inner walls in the apex-side region is halved and a lower-side center position at which a gap between the inner walls in the lower-side region is halved.

<9> The fine hollow protruding tool as set forth in any one of the clauses <1> to <8>, wherein the fine hollow protrusions each have a wall thickness, on an upper face of the basal member, that is preferably from 0.004 to 0.4 mm inclusive, and more preferably from 0.008 to 0.25 mm.

<10> The fine hollow protruding tool as set forth in any one of the clauses <1> to <8>, wherein, in any vertical cross-section passing through an apex of the fine hollow protrusion, an angle formed by the perpendicular line passing through the apex and the outer wall of the fine hollow protrusion on the apex side is different from that on the basal member side, and the angle on the basal member side is larger than the angle on the apex side.

<11> The fine hollow protruding tool as set forth in the clause <10>, wherein a ratio θ3/θ4 of an angle θ3 formed by the perpendicular line passing through the apex and the outer wall on the apex portion side with respect to an angle θ4 formed by the perpendicular line and the outer wall on the basal member side is preferably from 0.05 to 0.6 inclusive, and more preferably from 0.1 to 0.5.

<12> The fine hollow protruding tool as set forth in the clause <10> or <11>, wherein a ratio H3/H1 of a height H3 from an upper face of the basal member to a step with respect to a projecting height H1 of the fine hollow protrusion is preferably from 0.05 to 0.6 inclusive, and more preferably from 0.1 to 0.5.

<13> The fine hollow protruding tool as set forth in any one of the clauses <10> to <12>, wherein the fine hollow protrusions each have a wall thickness at a step that is preferably from 0.005 to 0.5 mm inclusive, and more preferably from 0.01 to 0.3 mm.

<14> The fine hollow protruding tool as set forth in any one of the clauses <10> to <13>, wherein the fine hollow protrusions each have a wall thickness, on an upper face of the basal member, that is preferably from 0.01 to 0.8 mm inclusive, and more preferably from 0.02 to 0.5 mm.

<15> The fine hollow protruding tool as set forth in any one of the clauses <1> to <14>, wherein the fine hollow protrusions each have a projecting height that is preferably from 0.01 to 10 mm inclusive, and more preferably from 0.02 to 5 mm.

<16> The fine hollow protruding tool as set forth in any one of the clauses <1> to <15>, wherein the fine hollow protrusions each have a wall thickness at a tip thereof that is preferably from 0.001 to 0.1 mm inclusive, and more preferably from 0.003 to 0.05 mm.

<17> The fine hollow protruding tool as set forth in any one of the clauses <1> to <16>, wherein the fine hollow protrusions each have a wall thickness, at a position where a projecting height thereof is halved, that is preferably from 0.001 to 0.1 mm inclusive, and more preferably from 0.003 to 0.05 mm.

<18> The fine hollow protruding tool as set forth in any one of the clauses <1> to <17>, wherein the fine hollow protrusions each have a tip diameter that is preferably from 1 to 500 µm inclusive, and more preferably from 5 to 300 µm.

<19> The fine hollow protruding tool as set forth in any one of the clauses <1> to <18>, wherein the basal member has a thickness that is preferably from 0.01 to 1.0 mm inclusive, and more preferably from 0.02 to 0.7 mm.

<20> The fine hollow protruding tool as set forth in any one of the clauses <1> to <19>, wherein a ratio (R1/H1) of a radius of curvature R1 at the base portion of the fine hollow protrusion on the basal member with respect to the projecting height H1 of the fine hollow protrusion is preferably from 0.01 to 0.5 inclusive, and more preferably from 0.02 to 0.3.

<21> The fine hollow protruding tool as set forth in any one of the clauses <1> to <20>, wherein a ratio (R2/H1) of a radius of curvature R2 at the entrance portion of the fine hollow protrusion, on an opposite face of the basal member opposite from a face from which the fine hollow protrusion projects, with respect to the projecting height H1 of the fine hollow protrusion is preferably from 0.01 to 0.4 inclusive, and more preferably from 0.02 to 0.25.

<22> The fine hollow protruding tool as set forth in any one of the clauses <1> to <21>, wherein the fine hollow protruding tool is a microneedle array.

INDUSTRIAL APPLICABILITY

According to the present invention, it is possible to reduce pain when piercing the skin and to make the fine hollow protruding tool unlikely to break.

The invention claimed is:

1. A fine hollow protruding tool comprising a basal member and a fine hollow protrusion which project from the basal member, the fine hollow protrusion having an opening portion on a tip side thereof and an interior space formed to link to the opening portion,
   wherein, in any vertical cross-section passing through an apex of the fine hollow protrusion,
   a wall thickness in an apex-side region on the apex side is thinner than a wall thickness in a lower-side region that is closer to the basal member than the apex-side region, and a gap between inner walls in the apex-side region is smaller than a gap between the inner walls in the lower-side region,
   a base portion of the fine hollow protrusion projecting from the basal member has a curvature, and
   an entrance portion to the fine hollow protrusion, on an opposite face of the basal member opposite from a face from which the fine hollow protrusion projects, has a curvature,
   wherein the basal member and the fine hollow protrusion of the fine hollow protruding tool are formed of a thermoplastic resin.

2. The fine hollow protruding tool according to claim 1, wherein the wall thickness in the apex-side region is uniform around an entire circumference.

3. The fine hollow protruding tool according to claim 1, wherein, in any vertical cross-section passing through the apex of the fine hollow protrusion,
   an angle formed by a perpendicular line passing through the apex and an outer wall of the fine hollow protrusion is larger than an angle formed by the perpendicular line and an inner wall of the fine hollow protrusion.

4. The fine hollow protruding tool according to claim 3, wherein a ratio (θ2/θ1) of an angle θ2 formed by the perpendicular line passing through the apex and the outer wall with respect to an angle θ1 formed by the perpendicular line passing through the apex and the inner wall is from 0.03 to 90.

5. The fine hollow protruding tool according to claim 3, wherein an angle θ1 formed by the perpendicular line passing through the apex and the inner wall is 0.5 to 30 degrees.

6. The fine hollow protruding tool according to claim 3, wherein an angle θ2 formed by the perpendicular line passing through the apex and the outer wall is 1 to 45 degrees.

7. The fine hollow protruding tool as set forth in claim 1, wherein, in any vertical cross-section passing through the apex of the fine hollow protrusion,
a perpendicular line passing through the apex passes through an apex-side center position at which a gap between the inner walls in the apex-side region is halved and a lower-side center position at which a gap between the inner walls in the lower-side region is halved.

8. The fine hollow protruding tool according to claim 1, wherein the fine hollow protrusion has a wall thickness, on an upper face of the basal member, that is from 0.004 to 0.4 mm.

9. The fine hollow protruding tool according to claim 1, wherein, in any vertical cross-section passing through the apex of the fine hollow protrusion,
an angle formed by a perpendicular line passing through the apex and an outer wall of the fine hollow protrusion on the apex side is different from that on the basal member side, and an angle on the basal member side is larger than an angle on the apex side.

10. The fine hollow protruding tool according to claim 9, wherein a ratio θ3/θ4 of an angle θ3 formed by the perpendicular line passing through the apex and the outer wall on the apex portion side with respect to an angle θ4 formed between the perpendicular line and the outer wall on the basal member side is from 0.05 to 0.6.

11. The fine hollow protruding tool according to claim 9, wherein the outer wall has a two-step structure consisting of an apex portion-side outer wall located on the apex side and formed in the shape of a straight line, and a basal member-side outer wall located on the basal member side and formed in the shape of a straight line with a degree of inclination different from that of the apex portion-side outer wall, and
a ratio H3/H1 of a height H3 from an upper face of the basal member to a step of the two-step structure with respect to a projecting height H1 of the fine hollow protrusion is from 0.05 to 0.6.

12. The fine hollow protruding tool according to claim 9, wherein the outer wall has a two-step structure consisting of an apex portion-side outer wall located on the apex side and formed in the shape of a straight line, and a basal member-side outer wall located on the basal member side and formed in the shape of a straight line with a degree of inclination different from that of the apex portion-side outer wall, and
the fine hollow protrusions each have a wall thickness at a step of the two-step structure that is from 0.005 to 0.5 mm.

13. The fine hollow protruding tool according to claim 9, wherein the fine hollow protrusion has a wall thickness, on an upper face of the basal member, that is from 0.01 to 0.8 mm.

14. The fine hollow protruding tool according to claim 1, wherein the fine hollow protrusion has a projecting height that is from 0.01 to 10 mm.

15. The fine hollow protruding tool according to claim 1, wherein the fine hollow protrusion has a wall thickness at a tip thereof that is from 0.001 to 0.1 mm.

16. The fine hollow protruding tool according to claim 1, wherein the fine hollow protrusion has a wall thickness, at a position where a projecting height thereof is halved, that is from 0.001 to 0.1 mm.

17. The fine hollow protruding tool according to claim 1, wherein the fine hollow protrusion has a tip diameter that is from 1 to 500 µm.

18. The fine hollow protruding tool according to claim 1, wherein the basal member has a thickness that is from 0.01 to 1.0 mm.

19. The fine hollow protruding tool according to claim 1, wherein a ratio (R1/H1) of a radius of curvature R1 at the base portion of the fine hollow protrusion on the basal member with respect to a projecting height H1 of the fine hollow protrusion is from 0.01 to 0.5.

20. The fine hollow protruding tool according to claim 1, wherein a ratio (R2/H1) of a radius of curvature R2 at the entrance portion to the fine hollow protrusion, on an opposite face of the basal member opposite from a face from which the fine hollow protrusion projects, with respect to a projecting height H1 of the fine hollow protrusion is from 0.01 to 0.4.

21. The fine hollow protruding tool according to claim 1, wherein the fine hollow protruding tool is a microneedle array.

22. The fine hollow protruding tool according to claim 1, wherein the interior space and an outer shape of the fine hollow protrusion are each formed in a truncated conical shape.

23. The fine hollow protruding tool according to claim 22, wherein, in the interior space formed in the truncated conical shape, a circular shape defined by the inner wall in a horizontal cross-section in the apex-side region is concentric with a circular shape defined by the inner wall in a horizontal cross-section in the lower-side region.

24. The fine hollow protruding tool according to claim 1, wherein
a ratio (R1/H1) of a radius of curvature R1 at the base portion of the fine hollow protrusion on the basal member with respect to a projecting height H1 of the fine hollow protrusion is from 0.01 to 0.5,
a ratio (R2/H1) of a radius of curvature R2 at the entrance portion to the fine hollow protrusion, on an opposite face of the basal member opposite from a face from which the fine hollow protrusion projects, with respect to the projecting height H1 of the fine hollow protrusion is from 0.01 to 0.4,
the radius of curvature R1 is smaller than the radius of curvature R2, and
the fine hollow protruding tool is used for delivering an agent from an outside to an inside of the fine hollow protruding tool.

25. The fine hollow protruding tool according to claim 24, wherein the interior space is formed in a truncated conical shape.

* * * * *